United States Patent
Ross et al.

(10) Patent No.: US 7,572,357 B2
(45) Date of Patent: Aug. 11, 2009

(54) CHIRAL TEMPERATURE GRADIENT FOCUSING

(75) Inventors: David J. Ross, Silver Spring, MD (US); Wyatt N. Vreeland, Washington, DC (US); Karin M. Balss, Basking Ridge, NJ (US)

(73) Assignee: The United States of America as represented by the Secretary of Commerce, the National Institute of Standards and Technology, Washington, DC (US)

( * ) Notice: Subject to any disclaimer, the term of this patent is extended or adjusted under 35 U.S.C. 154(b) by 846 days.

(21) Appl. No.: 11/039,955

(22) Filed: Jan. 24, 2005

(65) Prior Publication Data

US 2005/0258040 A1 Nov. 24, 2005

Related U.S. Application Data

(63) Continuation-in-part of application No. 10/197,331, filed on Jul. 18, 2002, now Pat. No. 7,029,561.

(60) Provisional application No. 60/307,691, filed on Jul. 25, 2001, provisional application No. 60/323,404, filed on Sep. 19, 2001, provisional application No. 60/544,126, filed on Feb. 12, 2004.

(51) Int. Cl.
*G01N 27/447* (2006.01)
(52) U.S. Cl. .................. 204/452; 204/450; 204/451
(58) Field of Classification Search ......... 204/450–455, 204/600–605
See application file for complete search history.

(56) References Cited

U.S. PATENT DOCUMENTS 7,029,561 B2 * 4/2006 Ross et al. ............... 204/451

OTHER PUBLICATIONS

Balss et al., "Simultaneous Concentration and Separation of Enantiomers with Chiral Temperature Gradient Focusing," Anal. Chem. 2004, 76, 7243-7249.*
Ross et al., "Microfluidic Temperature Gradient Focusing," Anal. Chem. 2002, 74, 2556-2564.*

* cited by examiner

*Primary Examiner*—Alex Noguerola
(74) *Attorney, Agent, or Firm*—Stites & Harbison PLLC; Ross F. Hunt, Jr.; Stephen J. Weyer

(57) ABSTRACT

A method and device are provided for concentrating and separating materials in fluids within a fluidic device having a fluid conduit such as a channel or capillary. The concentration is achieved by balancing the electrophoretic velocity of a material against the bulk flow of fluid in the presence of a temperature gradient. An additive is added to the fluid which interacts with the material and which modifies the normal electrophoretic mobility of the material. Using an appropriate fluid, the temperature gradient can generate a corresponding gradient in the electrophoretic velocity so that the electrophoretic and bulk velocities sum to zero at a unique position along the conduit and the material will be focused at that position. The method and device may be adapted for use with a variety of materials including fluorescent dyes, amino acids, proteins, DNA and to concentrate a dilute material.

29 Claims, 8 Drawing Sheets

PRIOR ART

CHIRAL TEMPERATURE GRADIENT FOCUSING

CROSS-REFERENCE TO RELATED APPLICATIONS

This application is a continuation-in-part of U.S. patent application Ser. No. 10/197,331 filed on Jul. 18, 2002, now U.S. Pat. No. 7,029,561 which claims benefit of the filing date of both Provisional Patent Application Nos. 60/307,691, filed on Jul. 25, 2001, and 60/323,404, filed on Sep. 19, 2001 and this application also claims benefit of the filing date of Provisional Patent Application No. 60/544,126 filed on Feb. 12, 2004.

STATEMENT REGARDING FEDERALLY SPONSORED RESEARCH

This invention was made by employees of the United States Government and may be manufactured and used by or for the Government for governmental purposes without the payment of any royalties.

FIELD OF THE INVENTION

The present invention relates to a method for electrokinetic focusing of materials in a fluid, and in particular, methods for electro-focusing materials in fluidic devices using electric field gradients.

BACKGROUND OF THE INVENTION

Over the past decade a great deal of research has been focused on the development of technology related to micro-total-analytical systems. This technology is based on the concept of a series of microfluidic channels also known as microchannels for the movement, separation, reaction, and/or detection of various materials, such as chemicals or biological compounds like amino acids, proteins, and DNA.

One disadvantage with prior microfluidic devices is that there is frequently a mismatch between the extremely small quantities of sample material used for analysis and the often much larger quantities needed for loading the material into the microfluidic device and transporting it to the point of analysis. For example, a typical analysis sample may be around one nanoliter or less of a liquid containing one or more materials that is injected into a separation channel and then separated electrokinetically as it moves down the channel to a detection region. However, the channels used to transport the sample materials to the injection point are typically also filled with the sample, thus increasing the required amount of the sample by a factor of 100 or more. In addition, the sample is typically loaded onto the microfluidic device into a reservoir from a pipette so that in all, approximately 99.9% of the sample is discarded as waste.

One way of addressing the problem of requiring a large amount of sample material for analysis due to the inefficiencies of conventional devices which result in wasted sample is to use one of any number of focusing techniques to concentrate the materials. In the context of this disclosure, focusing refers to methods for manipulating the velocity of a material and thereby causing it to move towards a position at which the velocity is zero. At the zero velocity position the material will accumulate and increase in concentration, i.e., it will become focused. In addition, the location of the zero velocity position is often dependent upon some characteristic of the material being focused, so that different materials are focused at different positions, and can thereby be separated from a mixture of materials.

Prior focusing methods include isoelectric focusing; electromobility focusing; counteracting chromatographic electrophoresis; temperature gradient focusing, disclosed in U.S. patent application Publication No. 2003/0019752, herein incorporated by reference; and most recently, mixing reactions by temperature gradient focusing, disclosed in co-pending U.S. patent application Ser. No. 10/039,904 herein incorporated by reference; and micellar affinity gradient focusing, disclosed in U.S. patent application Publication No. 2004/0206626, herein incorporated by reference. With the exception of the recently described micellar affinity gradient focusing method, the focusing methods all separate different materials based upon their electrophoretic properties, e.g., mobility in the case of electromobility focusing and temperature gradient focusing, and the isoelectric point in the case of isoelectric focusing.

Electric field gradient focusing is one focusing technique which can be used to concentrate a material at a given position within a microfluidic device before the analysis or other step. Further, the electric field gradient can be used to concentrate all of a selected material at the beginning of the separation channel so that very little of the material would be wasted.

Electric field gradient focusing is accomplished by the application of an electric field gradient within a microchannel. In response to the electric field gradient, there is a corresponding gradient in the electrophoretic velocity of any ionic material within the microchannel. The total velocity of the material is the sum of its electrophoretic velocity and the bulk fluid velocity. If these two components of the velocity are in opposite directions, they can be balanced so that the material will have zero total velocity.

When there is a gradient in the electrophoretic velocity, the balance between the bulk fluid velocity and the electrokinetic velocity can occur at a single position along the microchannel and therefore can result in focusing of the material at that position. Typically, the electric field gradient used in focusing is generated by the external manipulation of the electric field in the middle of the microchannel through the use of conducting wires, salt bridges, porous membranes, or other structures that will pass electric current but will restrict the flow of bulk fluid and the materials that are to be focused.

Several recent developments with regard to focusing methods in microfluidics, and in particular, the use of electric field gradients, have been made. A description of related methods of focusing can be found in C. F. Ivory, W. S. Koegler, R. L. Greenlee, and V. Surdigio, Abstracts of Papers of the American Chemical Society 207, 177-BTEC (1994); C. F. Ivory, Separation Science and Technology 35, 1777 (2000); Z. Huang and C. F. Ivory, Analytical Chemistry 71, 1628 (1999); W. S. Koegler and C. F. Ivory, Journal of Chromatography a 726, 229 (1996); and P. H. Ofarrell, Science 227, 1586 (1985), all of which are hereby incorporated by reference.

To illustrate the basic principles disclosed in these publications, reference is made to FIG. 1(a) which depicts a length of fluid-filled microchannel of constant cross-sectional area with an electrode, denoted 4, in the middle, and two further electrodes at each end, denoted 3 and 5, so that the voltages $V_1$, $V_3$ at the ends and the voltage $V_2$ at the middle of the channel can be controlled. A single species of negatively charged ionic material is present in the fluid that is within the microchannel. The electrical connection, represented as electrode 4, can be accomplished with a simple metal wire as depicted in FIG. 1(a), or through a more complicated structure consisting of additional fluid channels and porous membrane structures or salt bridges.

The electric field in the section 1, i.e., the channel between electrodes 3 and 4 is $E_1=(V_2-V_1)/(l/2)$ and the electric field in section 2, i.e., between electrodes 4 and 5, is $E_2=(V_3-V_2)/(l/2)$, where $V_1$, $V_2$, and $V_3$ are the voltages applied to the three electrodes 3, 4, and 5, and l is the length of the microchannel. If $E_1$ differs from $E_2$ as shown in FIG. 1(b), the electrophoretic velocity of the ionic material in the channel, $u_{EP}$, will be different in section 1 than in section 2. If an overall bulk fluid velocity, $u_B<0$, is applied, e.g., either electro-osmotic or pressure-driven, the bulk fluid velocity must be the same, due to continuity, in all parts of the microchannel. The total velocity of the ionic material, $u_T=u_B+u_{EP}$, will then be the sum of the electrophoretic and bulk velocities, which can differ in section 1 from section 2.

The use of the microchannel device of FIG. 1(a) for focusing of the ionic material is illustrated in FIG. 2 where $u_{T,1}>0>u_{T,2}$, so that the ionic material moves into the middle from both directions and is thus focused in the middle of the channel near electrode 4.

One major drawback to electric field gradient focusing is that the device tends to be difficult to construct and that it requires the control of voltage on an additional electrode, e.g. 4 of FIG. 1(a), that is used to apply the electric field gradient. In addition, if electrodes are used to generate electric field gradients, unwanted chemical products will be generated electrochemically at the fluid-electrode interface. If the electric field gradient is produced through the use of a salt bridge or membrane, the electrochemical products can be avoided, however only materials or chemical species that cannot pass through the membrane or salt bridge can be focused.

Two additional methods for concentrating a sample include sample stacking and field amplified sample injection in which a sample is concentrated as the sample crosses a boundary between low and high conductivity fluids. These methods can achieve preconcentration factors of 100 to 1000-fold although these methods require multiple fluids. Sweeping is yet another concentration method which is capable of a very high degree of sample concentration (e.g., up to 5000-fold), but is useful only for small molecular weight hydrophobic materials with a high affinity for a mobile micellar phase.

An additional technique for concentrating an ionic material includes isoelectric focusing. Isoelectric focusing is commonly used for the concentration and separation of proteins and involves the focusing of materials at their respective isoelectric points along a pH gradient.

Two examples of recent isoelectric focusing techniques are provided by U.S. Pat. No. 3,664,939 to Luner et al. and U.S. Pat. No. 5,759,370 to Pawliszyn. Both references relate to isoelectric focusing with pH gradients that are created by the application of a temperature gradient. Isoelectric focusing uses a pH gradient to focus materials and in particular proteins, at positions along the pH gradient where the local pH is equal to the isoelectric points of the materials. The isoelectric point is the pH at which the material has zero electrophoretic mobility, i.e., approximately zero charge. pH gradients for isoelectric focusing are typically generated using ampholyte mixtures or immobilized ampholytes in gels. The two above referenced patents are included here as examples of prior art uses of temperature gradients for focusing. It is, however, very unusual for isoelectric focusing to be done with a pH gradient generated using a temperature gradient.

One disadvantage of isoelectric focusing is that it is limited in application because it can only be used with materials having an accessible isoelectric point. Additionally, the concentration to which a protein can be focused with isoelectric focusing is severely limited due to the low solubility of most proteins at their isoelectric points.

In addition, further methods have been developed specifically to separate chiral species. Of the conventional methods of chiral separation, chiral capillary electrophoresis typically gives the best resolution, and is consequently widely used for analytical scale separations of chiral compounds and assays of enantiomeric purity. The major limitation of chiral capillary electrophoresis and of capillary electrophoresis in general is its poor detection limits, which are typically too high for the analysis of chiral compounds, e.g., drugs and drug metabolites in body fluids such as serum or urine. This major limitation is discussed throughout the scientific literature, including Scriba, G. K. E. *Electrophoresis* 2003, 24, 2409-2421; Bonato, P. S. *Electrophoresis* 2003, 24, 4078-4094; Hempel, G. *Electrophoresis* 2000, 21, 691-698; Chen, S. H.; Chen, Y. H. *Electrophoresis* 1999, 20, 3259-3268; and Altria, K. D.; Elder, D. *Journal of Chromatography A* 2004, 1023, 1-14.

Capillary electrophoresis is also commonly used to assess the enantiomeric purity of drugs. In order to detect and quantify a trace contaminant of one enantiomer against a large excess of the other, it is often necessary to reverse the order of peak migration so that the tail of the major enantiomer peak does not obscure the small impurity peak.

Isoelectric focusing and isoelectric trapping have also been used in conjunction with chirally selective additives for enantiomeric separations. However, these techniques are limited in their applicability because the chiral materials or molecules to be focused must be chemically derivatized so that 1) they have an isoelectric point, and 2) the isoelectric point is dependant on the degree of interaction with a chiral selector. The vast majority of pharmaceutical molecules do not have isoelectric points and so cannot be focused or separated with isoelectric focusing. Furthermore, most pharmaceutical molecules would not be amenable to the kind of chemical derivatization required for isoelectric focusing, see, e.g., Ogle, D.; Ho, A.; Gibson, T.; Rylatt, D.; Shave, E.; Lim, P.; Vigh, G. *Journal of Chromatography A* 2002, 979, 155-161; Rizzi, A. M.; Kremser, L. *Electrophoresis* 1999, 20, 3410-3416; Righetti, P. G.; Ettori, C.; Chafey, P.; and Wahrmann, J. P. *Electrophoresis* 1990, 11, 1-4 for a further discussion regarding the separation of chiral molecules using isoelectric focusing.

BRIEF SUMMARY OF THE INVENTION

The present invention is directed to overcoming the limitations of prior chiral separation methods by combining the high resolution of chiral capillary electrophoresis with the high concentration enhancement and low detection limits of temperature gradient focusing. According to one aspect of the present invention, there is provided a method for focusing a material using temperature gradient focusing in conjunction with a fluid additive, such as a chirally selective additive which modifies the electrophoretic mobility of materials in the fluid. The method may be conducted in fluid conduits such as channels, separation columns, tubes, microchannels, and capillary tubes. The concentration is achieved by balancing the electrophoretic velocity of a material against the bulk flow of fluid in the presence of a temperature gradient. Using an appropriate fluid in conjunction with a fluid additive which interacts with the material of interest, the temperature gradient generates a corresponding gradient in the electrophoretic velocity of the material so that the electrophoretic and bulk velocities sum to zero at a given position along the fluid conduit and the material will be focused at that position. The types of fluids that would typically be used include ionic aqueous solutions, ionic non-aqueous solutions, aqueous buffer solutions, and mixtures of aqueous and non-aqueous solutions. Because the present invention does not use semi-permeable structures such as salt bridges or membranes to form a velocity gradient, it may be adapted for use with any charged material, including small ions, large ions, fluorescent dyes, amino acids, proteins, DNA, cells, and particles and may provide up to or, in some instances, exceed a 10,000-fold concentration of a dilute material. Further, the present method can be used to separate stereoisomers of a material which have different affinities for the additive.

Since the present method combines temperature gradient focusing, in conjunction with a fluid additive that modifies the electrophoretic mobility of the material to be focused, the degree to which the electrophoretic mobility is modified will depend upon the strength of the interaction of the material with the additive. Consequently, two different materials that focus at the same position in temperature gradient focusing without the additive can potentially be focused at different positions in temperature gradient focusing with the additive if they differ in their interaction with the additive, and thus can be separated.

One aspect of the present invention concerns a method for directing materials contained in a fluid and which may include concentrating or separating materials present in the fluid. The method includes applying an electric field to a fluid containing one or more species of material to cause the materials to migrate electrophoretically. A temperature gradient is established in the fluid, thereby generating a gradient of the electrophoretic velocity of the materials. An additive is added to the fluid to modify the normal electrophoretic mobility of the materials based on the interaction between the materials and the additive. A flow is produced in the fluid such that the magnitudes and directions of the electric field, temperature gradient, and flow are such that at least one of the materials in the fluid will accumulate or be focused at a position along the gradient.

In various further alternative embodiments, the additive is a chiral selector, a non-ionic additive and forms a pseudostationary phase. In an additional alternative embodiment, the material is first focused without the additive which focuses all stereoisomers of a material at the same point. Subsequently, the additive is added to the fluid and the focusing continues, separating the stereoisomers.

According to another aspect of the present invention, a fluidic device includes a fluid conduit, a fluid disposed in the conduit and a source of one or more materials to be focused in fluid connection with the conduit. An electric power supply or other means is used to provide an electric field to the conduit. Heated or cooled blocks thermally coupled to the conduit or other means are used to generate a temperature gradient within the fluid conduit. A source of bulk fluid flow is used to provide a flow of fluid in the conduit. An additive is added to the fluid to modify the normal electrophoretic mobility of the materials based on the materials' interaction with the additive. In alternate, further embodiments, the fluid has either a temperature dependent ionic strength or a temperature dependent pH such that when a temperature gradient is applied to the fluid conduit, a gradient of the materials' electrophoretic velocity is established in the fluid present in the fluid conduit.

One advantage or feature of the present invention is provided by a technique that allows for simultaneous concentration and separation in a manner similar to isoelectric focusing but which is adoptable for use with any charged material and is not limited to materials with a specific isoelectric point or range of isoelectric points. Further, the temperature gradient focusing of the present invention can be used to achieve higher degrees of sample concentration, e.g., more than 10,000 fold concentration of a dilute material, when compared with any prior single sample preconcentration method.

A further feature of the present invention is that the electrophoretic velocity gradient is formed within the channel or capillary in response to the temperature gradient without the need for externally manipulated voltages or complicated and difficult to fabricate semi-permeable structures.

A further feature of the present invention is the ability thereof to focus and separate chiral stereoisomers. For example, with the addition of a chiral additive, the present focusing method allows for simultaneous separation and concentration of materials that cannot be separated using temperature gradient focusing based purely upon their electrophoretic mobilities. One benefit of being able to separate chiral stereoisomers is that many drugs and drug candidates are chiral and in most cases, one stereoisomer is more desired for drug use than the other. In some instances, one stereoisomer is a beneficial drug, whereas the other results in adverse side effects.

An additional advantage of the present invention for the separation of the stereoisomers of a chiral material is that it is very easy to reverse the positional order of the focused peaks corresponding to the different stereoisomers. This can be done simply by reversing the direction of the temperature gradient, the sign of the applied electric field, and the direction of the bulk fluid flow. As mentioned above, this can be beneficial for the analysis of the purity of chiral materials that are desired to contain only one stereoisomer.

Further features and advantages of the present invention will be set forth in, or apparent from, the detailed description of preferred embodiments thereof which follows.

BRIEF DESCRIPTION OF THE DRAWINGS

The invention will now be described in detail with respect to preferred embodiments with reference to the accompanying drawings, wherein.

plotted as a function of the distance along the microchannel of FIG. 3(a), where $\sigma(T)$ is the temperature dependent conductivity, $\sigma_0$ is a constant, and $\eta(T)$ is the temperature dependent viscosity.

plotted as a function of the distance along the microchannel of FIG. 4(a)

DETAILED DESCRIPTION OF THE INVENTION

Figure 1A:
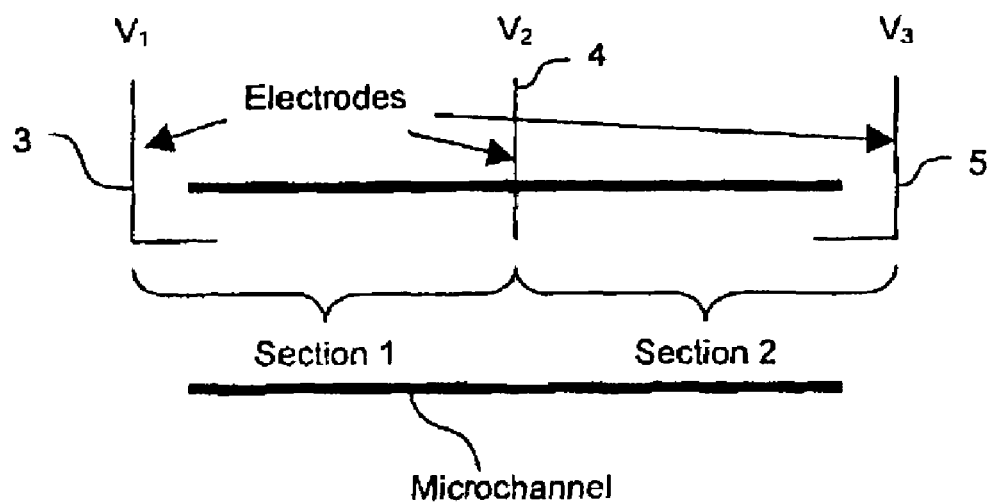
FIG. 1(a) is a schematic depicting a prior art microchannel device which provides for electric field gradient and FIG. 1(b) is a plot of the electric field versus distance (x) along the microchannel of FIG. 1(a)
Figure 1B:
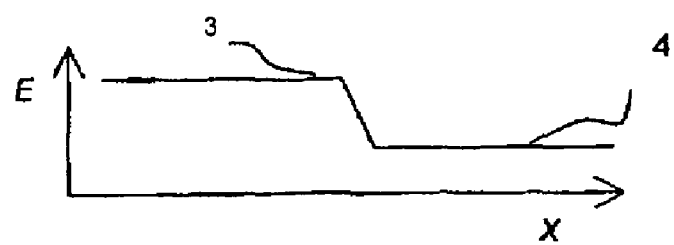
Figure 2:
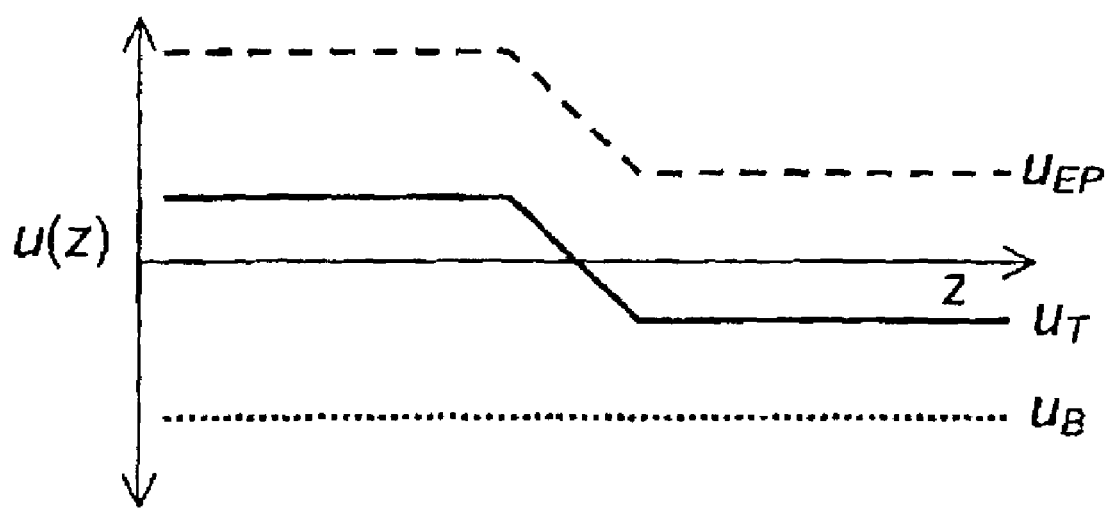
FIG. 2 is a plot of velocity versus distance along the microchannel of FIG. 1(a)

A material can be focused in a fluid conduit such as a channel or capillary when its total velocity is in opposite directions in different portions of the conduit, so that the material will move into the middle of the conduit and stop at a position where its velocity is zero. One way of accomplishing this is to cause the material to move with an electrophoretic velocity that varies along the length of the conduit. This can be accomplished by producing an electrophoretic velocity gradient along the conduit. If an electrophoretic velocity gradient is established, but the electrophoretic velocity is still in the same direction along the entire length of the conduit, a counter-balancing bulk flow can be applied to the fluid in the conduit, driven either by electroosmosis, pressure gradients, or both, so that the total velocity of the material, i.e., the vector sum of the bulk flow velocity and electrophoretic velocity of the material is equal to zero at some position along the conduit.

Temperature gradient focusing is a method for focusing materials that produces the required material electrophoretic velocity gradient through the application of a temperature gradient. In temperature gradient focusing, a fluid with a temperature dependent ionic strength is typically used to give an electrophoretic velocity that is temperature dependent. Then the electrophoretic velocity of the material can be altered in different portions of the conduit or capillary simply by heating or cooling different portions of the conduit. The application of a temperature gradient then results in an electrophoretic velocity gradient, which, with a counteracting bulk fluid flow, can be used for focusing. With temperature gradient focusing, different materials are focused at different positions and thereby separated based upon differences in their electrophoretic mobilities.

The present method includes temperature gradient focusing of a material with the addition of an additive that interacts with the materials to be focused, and thereby modifies their normal electrophoretic mobilities, thus changing the positions at which they focus. If two materials have the same or very nearly the same electrophoretic mobilities (as is the case for stereoisomers of a pharmaceutical molecule, for example), they can not normally be separated by temperature gradient focusing without the addition of an additive. If the additive interacts more strongly with one of the materials than the other however, they can be simultaneously concentrated and separated using the present method of temperature gradient focusing with an additive.

Further description of the present invention will now be made with reference to the drawings, and in particular to FIG. 3(a), where a fluid-filled microchannel 10 includes electrode connections 12, 14 at each end, one of which is connected to a high voltage source such as an electrical power supply and the other of which is electrically grounded. The velocity of a material in the microchannel 10 is given by the sum of its electrophoretic velocity, $u_{EP}$, and the bulk velocity, $u_B$, of the fluid:

$$u_T = u_{EP} + u_B.$$

If there is a gradient in the electrophoretic velocity, the bulk velocity can be adjusted so that the total velocity is equal to zero at a single point along the channel, and the material will be focused at a position around that point. The electrophoretic velocity of a material in the microchannel 10 is given by the product of the electric field, E, and the electrophoretic mobility of the material: $u_{EP} = E \cdot \mu_{EP}$.

Figure 3:
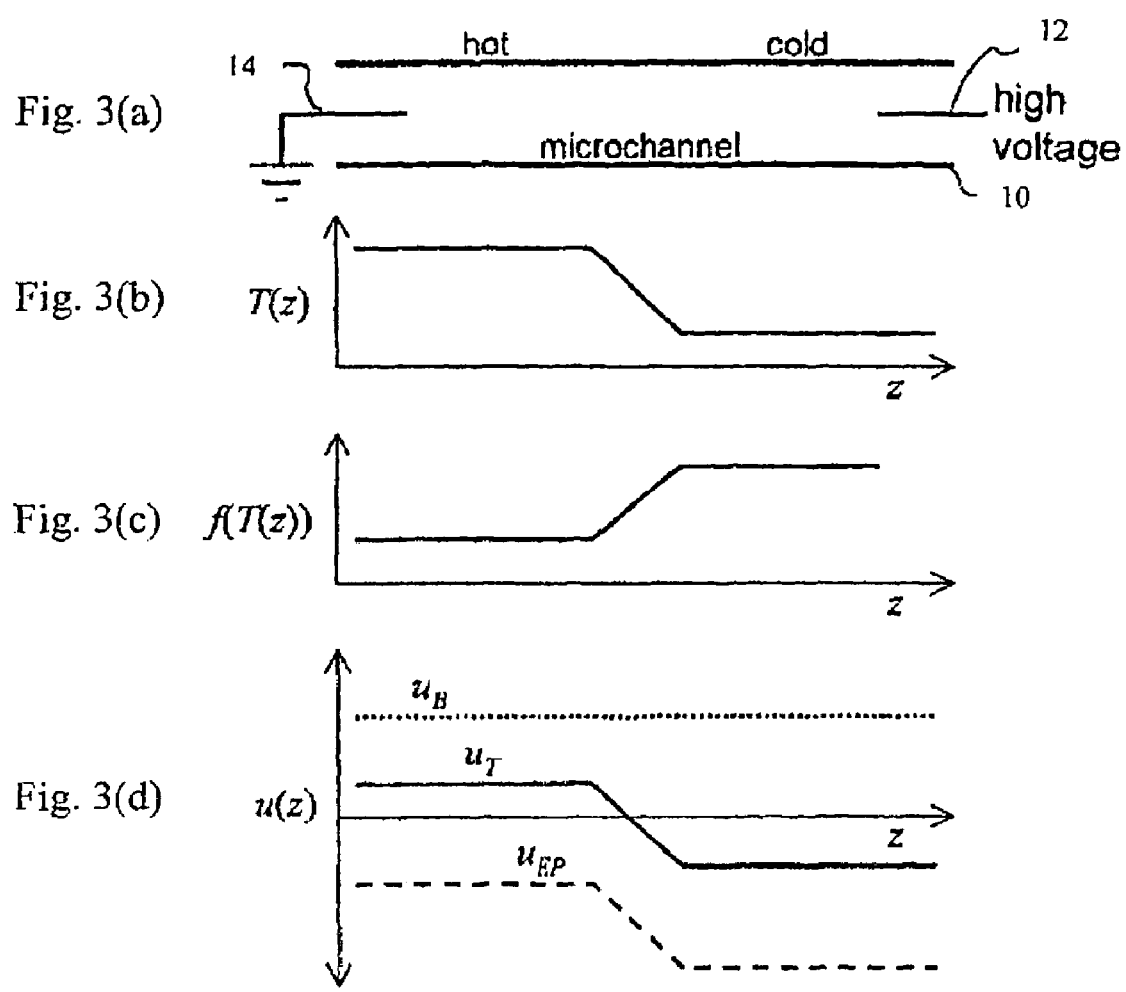
FIG. 3(a) is a schematic illustration of temperature gradient focusing and fluid conduit in the form of a microchannel in accordance with the present invention.
FIG. 3(b) depicts temperature distribution along the microchannel of FIG. 3(a)
FIG. 3(c) is a plot of the function $$f(T) = \frac{\sigma(20) \cdot \eta(20)}{\sigma(T) \cdot \eta(T)}$$
FIG. 3(d) is a plot depicting velocity as a function of distance along the microchannel.

A temperature gradient is applied along the length of the channel as shown in FIG. 3(b). This results in corresponding gradients in both the electric field E and the electrophoretic mobility $\mu_{EP}$.

The electric field in the microchannel 10 is given by:

$$E = \frac{I}{A \cdot \sigma},$$

where I is the electric current running through the microchannel 10, A is the channel cross-sectional area of the microchannel 10, and σ is the conductivity of the fluid. Since the conductivity of the fluid is almost always temperature-dependent, the electric field is also almost always temperature-dependent. Here, constant current is presumed because the current running through any given section of the microchannel 10 will be the same for all parts of the microchannel, whereas the voltage drop across a portion of the microchannel 10 and the electric field in the microchannel 10 will depend on the temperature of that portion. One skilled in the art will readily appreciate that the present temperature gradient focusing differs from electric field gradient focusing in that in electric field gradient focusing, the velocity gradient that is used for focusing results from a gradient in the electric field imposed by the addition or subtraction of current from a point or points within the microchannel.

Using microchannel 10, it is possible to manipulate the conductivity of the fluid by changing the temperature. Consequently, it is possible to produce electric field gradients in microfluidic devices, such as microchannel 10, through the application of a temperature gradient.

At fixed current density, the electric field in microchannel 10 is inversely proportional to the conductivity of the fluid in the microchannel. Most often, the primary temperature dependence of the conductivity is due to the variation of the fluid viscosity with temperature, so it can be written as $\sigma = \sigma_0 \cdot \eta(20)/(\eta(T) \cdot f(T))$, where σ is the conductivity, $\sigma_0$ is a constant, η(T) is the temperature dependent viscosity, and ƒ(T) is a dimensionless function that accounts for any other temperature dependence. Similarly, the temperature dependence of the electric field is given by $E = E_0 \cdot \eta(T) \cdot f(T)/\eta(20)$, where E is the electric field and $E_0$ is a constant.

For the types of fluids most commonly used microfluidic analysis (aqueous buffers), the function ƒ(T) is constant or only weakly dependent on temperature. However, it can be non-constant, i.e., variable, if, for example, the ionic strength of the fluid is temperature dependent. Advantageously, the fluids of the present invention are characterized by a non-constant $f(T)$.

The electrophoretic mobility of an ionic (e.g., material) species in the fluid is also dependent on the viscosity, and so can be written as $\mu_{EP} = \mu_0 \cdot \eta(20)/(\eta(T) \cdot f_{EP}(T))$, where $\mu_0$ and $f_{EP}(T)$ are defined in analogy to $\sigma_0$ and $f(T)$ where, for most materials, $f_E(T)$ will be constant. The electrophoretic velocity of the material can then be written as $u_{EP} = E_0 \cdot \mu_0 \cdot f(T)/f_{EP}(T)$. It should be noted that if $f(T)$ and $f_{EP}(T)$ have the same temperature dependence, e.g., they are both constant, then $u_{EP}$ will not be temperature dependent, and an electric field gradient produced in this way can not be used for focusing.

If, on the other hand, $f(T)$ and $f_{EP}(T)$ do not have the same temperature dependence, then temperature gradients will result in gradients in the electrophoretic velocity, which can be used for focusing as described above.

One skilled in the art will readily appreciate a major advantage of this present method over some other methods of preconcentration is that the concentrations of the background ions (those ions that are included in the fluid to provide a temperature-dependent ionic strength) are completely unaffected by the focusing. This results from the fact that if the background ions are considered as materials to be focused, then, by definition, $f_{EP}(T) = f(T)$ and there is no gradient in the electrophoretic velocities of the background ions.

Most commonly this technique would be implemented with a fluid characterized by a strongly temperature dependent $f(T)$ and with materials characterized by a constant or nearly constant $f_{EP}(T)$. However, the present temperature gradient focusing can also be implemented in a system in which $f(T)$ is constant and $f_{EP}(T)$ is not, or in which both $f(T)$ and $f_{EP}(T)$ are non-constant, but differ in their temperature dependence. One type of fluid that would have a temperature dependent $f(T)$, and could therefore be used for temperature gradient focusing, would be a fluid with a temperature dependent ionic strength.

One preferred fluid system is composed of 0.9 mol/L Tris (hydroxymethyl)aminomethane and 0.9 mol/L boric acid in water (0.9 M Tris-borate buffer), with an expected pH of about 8.7 (at room temperature). From measurements of the conductivity of the 0.9 M Tris-borate buffer and the known viscosity of water, the function $f(T)$ for 0.9 M Tris-borate buffer was determined to vary from 1 at 20° C. to 0.77 at 70° C.

The counterbalancing bulk flow can be applied electroosmotically if the electro-osmotic mobility does not differ too much from the electrophoretic mobility of the material to be focused. If the electro-osmotic mobility is written as $\mu_{EO} = \mu_{EO}^0 \cdot \eta(20)/\eta(T)$, then by adjusting the ratio of the lengths of the hot and cold channels, (assuming $f_{EP}(T)$=constant) focusing can be achieved if $f(cold)/f(hot) \leftarrow \mu_0/\mu_{EO}^0 < f(hot)/f(cold)$, where $f(hot) > f(cold)$ (If $f(hot) < f(cold)$, then the inequalities have the opposite sign). If x is the fraction of the total channel length that is hot, then focusing will occur if: $x \cdot j(hot)/f(cold)+(1-x) \leftarrow \mu_0/\mu_{EO}^0 < x+(1-x) \cdot f(cold)/f(hot)$, where $f(hot) > f(cold)$. By adjusting x, it is then possible to tune the range of material mobilities that are focused. In many cases, the electrophoretic and electroosmotic mobilities will not be so well balanced, and therefore although the bulk velocity will be largely due to electroosmosis, it must also be adjusted using an externally applied pressure gradient.

It should be noted that temperature gradient focusing can also be implemented in microchannels or other fluid conduits of non-constant cross-section. The final results are essentially unchanged, since in most instances, the dependence on the cross-sectional area of the channel cancels out in the equations. As a result, it is possible to generate the temperature gradient using Joule heating within the microchannel. This would serve to simplify the design and operation of a microfluidic device using this technique even further, since the focusing and the temperature gradient could be produced using the same voltage source and pair of electrodes as illustrated in FIG. 4(a).

Figure 4:
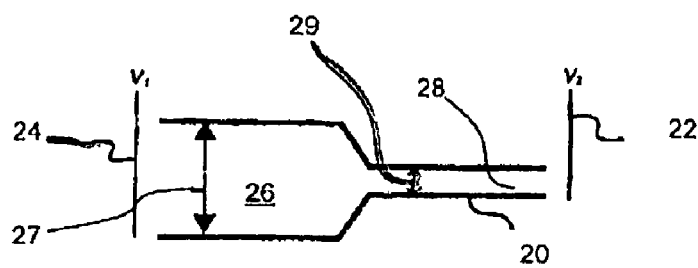
FIG. 4(a) is a schematic illustration of a microchannel for temperature gradient focusing created by Joule heating according to another embodiment of the present invention.
FIG. 4(b) depicts the temperature profile along a length of the microchannel of FIG. 4(a)
FIG. 4(c) is a plot of the function $$f(T) = \frac{\sigma(20) \cdot \eta(20)}{\sigma(T) \cdot \eta(T)}$$
FIG. 4(d) is a plot showing electrophoretic velocity, bulk velocity, and total velocity vs. distance along the microchannel of FIG. 4(a)
Figure 4:
Figure 4:
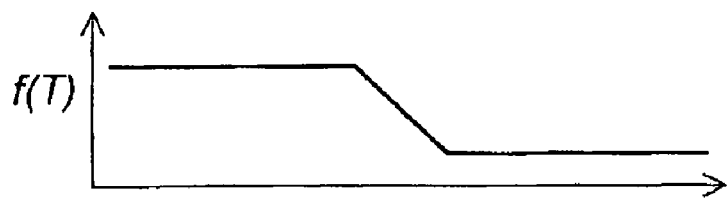
Figure 4:
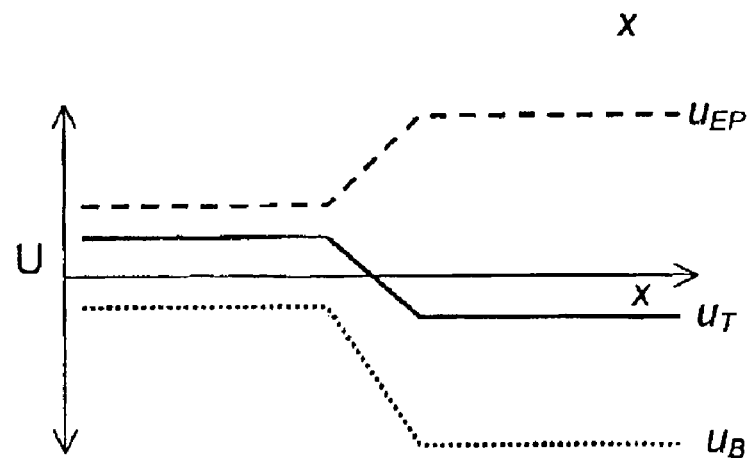

Microchannel 20 shown schematically in FIG. 4(a), has electrodes, 22, 24, and two sections, sections 26, 28, of different cross-sectional area. Section 26 has a cross-sectional area of 27 and section 28 has a cross-sectional area of 29. The electrical resistance per unit length of each section is given by: $R_i = 1/(\sigma \cdot A_i)$, where $\sigma$ is the conductivity of the fluid in the microchannel 20. When a current, I, is passed through the microchannel 20, the power per unit length dissipated through Joule heating in each section will be: $P_i = I^2 \cdot R_i = I^2/(\sigma \cdot A_i)$. In general, the resulting temperature in section 28 will be higher than that in section 26, as shown in FIG. 4(b): $T_2 > T_1$. The electric field in each section of the microchannel 20 is given by the current multiplied by the resistance per unit length: $E_i = I \cdot R_i = I/(\sigma \cdot A_i) = I \cdot \eta(T_i) \cdot f(T_i)/(\sigma_0 \cdot h(20) \cdot A_i)$.

The electrophoretic velocity of a material in each section of the channel is: $u_{EP}^i = \mu_0 \cdot f(T_i) \cdot I/(\sigma_0 \cdot f_{EP}(T) \cdot A_i)$. If a bulk flow velocity is applied along the channel, it will not be the same in each section, but will instead be given by $u_B^i = u_B^0/A_i$, where, $u_B^0$ is a constant. The ratio of the electrophoretic velocity to the bulk velocity is then given by: $u_i^{ratio} = \mu_0 \cdot f(T_i) \cdot I/(\sigma_0 \cdot f_{EP}(T) \cdot u_B^0) \equiv u_0^{ratio} \cdot f(T_i)/f_{EP}(T)$ via adjusting $u_B^0$ so that $|u_1^{ratio}| > 1 > |u_2^{ratio}|$ as shown in FIG. 4(d), which can result in focusing. Because the ratio of the electrophoretic velocity to the bulk velocity does not depend on the cross-sectional areas of the two sections, the same considerations as above apply if bulk flow is applied electroosmotically.

Joule heating may be used to generate the temperature gradient in the microchannel device of FIG. 4(a). The following is a non-limiting example demonstrating Joule heating of a microchannel of the type shown in FIG. 4(a).

The microchannel used for this demonstration was similar to the one shown schematically in FIG. 4(a). The width, i.e., cross sectional area 29, of the narrow channel, i.e., section 28, was about 70 µm, and the width of the wide section, i.e., section 26, cross sectional area 27 was about 350 µm. The length of the tapered portion of the channel was about 500 µm. The depth of all portions of the channel was about 30 µm. The total length of the microchannel was about 2 cm, with the length of the section 28 divided by the total length, x≅0.8. Access to each end of the microchannel was provided by a 3 mm hole through the lid piece of the microchannel.

0.9 M Tris-borate buffer was used as the fluid for temperature gradient focusing. An 8 µmol/L solution of carboxyfluorescein in 0.9 M Tris-borate buffer was prepared. The material to be concentrated was the carboxyfluorescein. Detection of the material was performed using a fluorescence microscope and CCD cameras. Simultaneous color and grayscale images were obtained.

To demonstrate gradient focusing using Joule heating, the microchannel was filled with the caboxyfluorescein solution and 1900 V was applied along its length using a high voltage power supply and platinum electrodes, with the positive voltage $V_2$ applied to the narrow end via electrode 22, and the wide end held at ground at electrode 24.

After 6 min., the carboxyfluorescein was highly concentrated at the junction between sections 26 and 28 of the microchannel 20. The concentration factor achieved by using this example was typically about 100-fold per minute.

Figure 5:
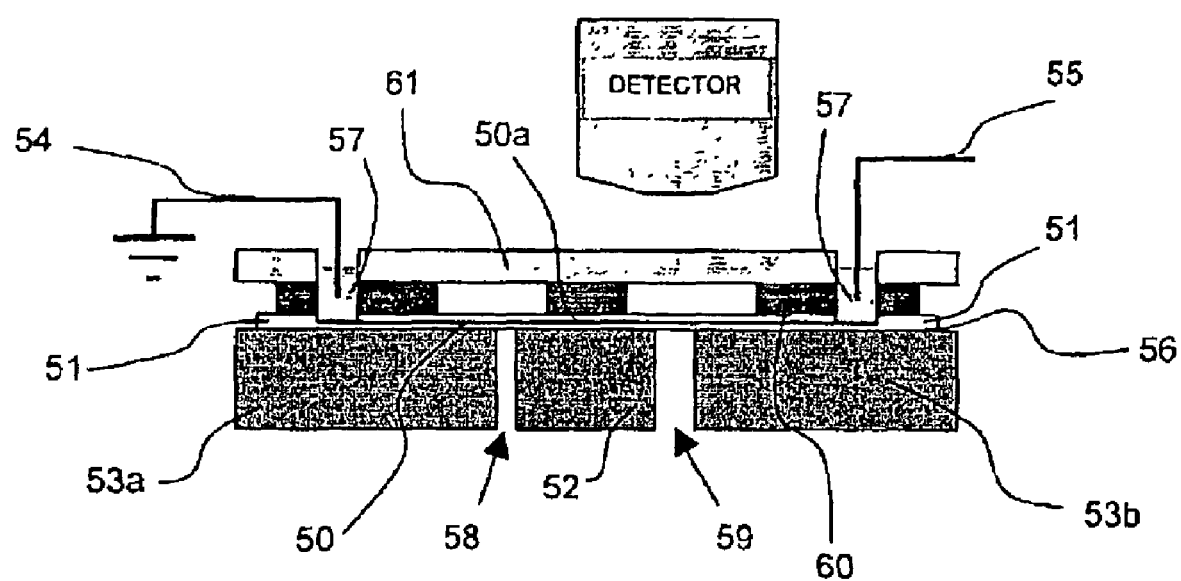
FIG. 5 is a schematic drawing of a fluidic device according to further embodiment of the present invention.

Referring now to FIG. 5, in order to have better control of the temperature gradient, experiments were done using three temperature zones, two cold zones provided by cooling copper blocks 53a, 53b covering much of the ends of the microchannel 50, and one hot zone provided by heated copper block 52. The microchannel 50 was made out of thin (125 μm) sheets of poly(carbonate) substrate 51, which were pressed onto the copper blocks 52, 53a, 53b. Thermal contact between the poly(carbonate) and the copper blocks was insured using a thermally conductive adhesive 56. The copper blocks 52, 53a, 53b were arranged so that there was a 1 mm gap 58 between the heated copper block 52 and the cooling copper block 53a and a 2 mm gap 59 between heated copper block 52 and the cooling copper block 53b.

Microchannel 50 also includes electrodes 55, 54, fluid reservoirs 57, and a narrow hot zone 50a near the middle of the microchannel 50. The heated copper block 52 was heated using a small high-power resistor embedded into the copper and its temperature was regulated using a PID temperature controller (Omega Engineering Inc, Stamford, Conn.). To regulate the temperature of the cold zones, ¼ inch diameter holes were drilled through the cooling copper blocks 53a, 53b and cold water from a thermostatted bath (Neslab, Portsmouth, N.H.) was passed through them.

Thin polycarbonate microchannel chips, i.e. substrate 51 was attached to the copper blocks 52, 53a, 53b using thermally conductive adhesive 56 in the form of transfer tape (3M). The substrate 51 was pressed against the copper blocks 52, 53a, 53b from above with 3 mm thick PDMS (Sylgard 184, Dow Corning, Midland, Mich.) gaskets 60 and a 2 mm thick acrylic (Acrylite OP-4, Cyro Industries, Mt. Arlington, N.J.)) top plate 61, which was secured to the outer copper clocks using nylon screws (not shown).

During temperature gradient focusing, a voltage potential is applied to electrode 55 and electrode 54 is set to ground using a high voltage power supply. In most cases, the electrophoretic and electroosmotic mobilities are not sufficiently balanced, so that an externally applied pressure gradient must be applied to microchannel 50 to allow microchannel 50 to provide focusing and separation of different types of materials: small dye molecules, amino acids, proteins, DNA, colloidal particles, and cells. There are many possible means for applying the necessary pressure gradient, including the use of pneumatic pressure controllers, and adjusting the volume of fluid contained in the reservoirs 57 to take advantage of gravitational and/or capillary (surface tension-driven) forces.

The microchannel 50 may be formed by imprinting with a micro machined silicon template and then sealed with a similar material according to the method disclosed in Ross, D.; Gaitan, M.; Locascio, L. E., *Analytical Chemistry* 2001, 73, 4117-23, herein incorporated by reference.

The copper block arrangement was also used to determine the degree of focusing that could ultimately be reached with temperature gradient focusing. Beginning with a 8 nM solution of Oregon Green 488 carboxylic acid in 0.9 M Trisborate, 100 min of focusing resulted in a focused plug of Oregon Green 488 carboxylic acid with a peak concentration over 80 μM—a greater than 10000-fold increase in concentration.

It will become readily apparent to one of ordinary skill in the art that the present method provides for use in numerous applications. For example, temperature gradient focusing could be used as a preconcentration step before an analysis or separation or as a simultaneous concentration and separation technique. In addition, temperature gradient focusing could be used for preparative scale separation of different materials or different enantiomers if the focused material or materials are collected after focusing.

In addition, temperature gradient focusing may be used with any charged material and not just small molecules. For example, the materials may include larger molecules such as proteins and DNA, or even particles and cells. Further, the present method can be used with particles to create packed beds of particles or cells for use in other analysis steps. In addition, the present method can be adapted for use to sort particles or cells by electrophoretic mobility.

In one separation mode, the bulk velocity could be ramped over time to scan focused sample peaks past a fixed detector, e.g. the detector shown in FIG. 5. This would produce results similar to capillary electrophoresis but the widths of the sample peaks would be determined by the applied gradients and the peak heights would be determined by how long a given peak was in the focusing "window". If the ramp speed were halved, the peak heights would all be doubled, so that the ramp rate could be chosen dependent on the concentration limit of detection necessary. Alternatively, the focusing window could remain fixed and a scanning or imaging detector could be used to locate the separate peaks.

In a further embodiment, the method may be adapted for a system where temperature dependence is due to something other than the ionic strength. An example is a system having $f(T)$ constant but $f_{EP}(T)$ not constant, or variable. One way to accomplish this would be to use a fluid with a temperature dependent pH. In such a system, this embodiment of the present invention is similar to isoelectric focusing schemes. However, the present invention differs from isoelectric focusing in that, in the present system, an opposing fluid flow is applied so that materials are focused at a pH other than their isoelectric points.

When using any of the embodiments of the present method, operating parameters which include voltage, bulk flow rate, and temperature of the different zones may be held constant with time or varied with time to affect the position and width of focused sample peaks. Varying of parameters may be accomplished using any of a number of methods which include the methods previously described above in which the focused sample peaks are scanned past a fixed detector.

Advantageously, in order to achieve the fastest accumulation of material in the focused peak, the highest possible voltage should be used. However, a higher applied voltage requires a faster bulk flow which can result in greater dispersion, i.e., wider focused peaks, which is disadvantageous for separation and for achieving pre-concentration of a sample to a high concentration in a very narrow peak. Therefore, a high voltage and fast bulk flow could be used for the initial accumulation of material into a relatively broad peak, and the voltage flow and flow rate could then be reduced to the values which give the narrowest peaks. Further, temperature gradients could be turned on and off to first concentrate the sample and then release the focused peak and allow it to flow on down the channel. Further, the temperature gradient can be adjusted to be linear or nonlinear, and the temperature gradient may be monotonic or non-monotonic. Thus, operating parameters may be adjusted to achieve the desired results.

While the previously disclosed embodiments are directed to a microchannel or microfluidic device, the present method may be adapted for incorporation for use with substantially larger channels which may include millimeter and centimeter if not larger in dimension which should now be apparent to one of ordinary skill in the art. Because temperature gradient focusing uses low conductivity fluids, one ban adapt the present method for use in much larger scale geometries than the micron-sized channels and capillaries described in detail herein.

Figure 6:
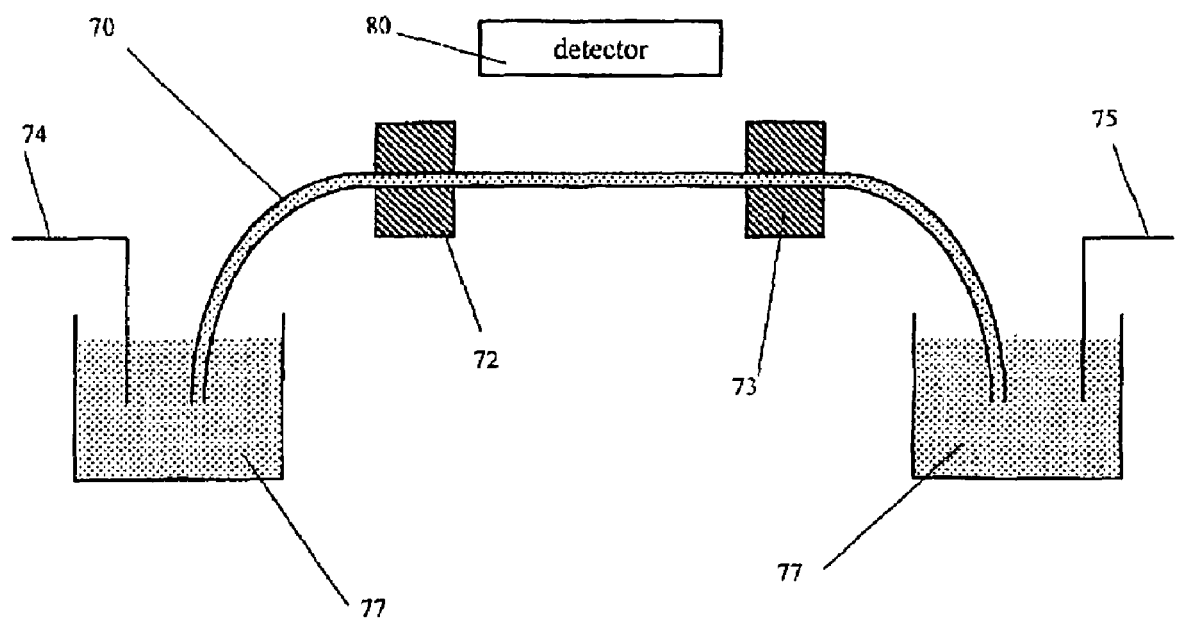
FIG. 6 is a schematic drawing of a capillary fluidic device according to an alternate embodiment of the present invention.

Further, the previously described method can be adapted for use in modified capillary fluidic systems known to one of ordinary skill in the art. FIG. 6 depicts a capillary fluidic system having a capillary tube 70 spanning between two fluid reservoirs 77. Two temperature blocks, denoted as heated block 72 and cooling block 73 are located along the length of the capillary tube 70 to provide a desired temperature gradient in the capillary tube 70. Alternatively, temperature blocks being both cooling, both heated, both at ambient temperature, or any combination, thereof, may be substituted to provide the desired temperature gradient.

The fluid reservoirs 77 contain a fluid with temperature dependent ionic strength. Electrodes 74, 75 are connected at one end to a power supply and on the other end, are in contact with the fluid in the reservoirs 77. The power supply applies a driving voltage through the capillary tube 70. A source of bulk flow is driven either by electro-osmosis with the applied driving voltage, by a pressure gradient applied, e.g. by a pump, or a combination of the two. Detector 80 is used to detect materials present in the fluid.

In a specific chiral temperature gradient method of the present invention, one or more additives are added to the fluid to modify the normal electrophoretic mobility of the materials based on the interaction between the material and the additive. In one implementation, the additive is a chiral selector such as a cyclodextrin, in which case the method can be used for the focusing and separation of stereoisomers with respect to the chirality of the material. This method can be employed in the pharmaceutical industry as drug compounds are often chiral where one enantiomer may have a therapeutic effect while the other enantiomer is not efficacious, and is sometimes harmful. The chiral selectors that could be used with this new method include all of the many chiral selectors commonly used in chiral capillary electrophoresis such as alpha-cyclodextrin, beta-cyclodextrin, gamma-cyclodextrin, heptakis-O-methyl beta-cyclodextrin, heptakis(2,6-di-O-methyl) beta-cyclodextrin, heptakis(2,3,6-tri-O-methyl) beta-cyclodextrin, hydroxyethyl beta-cyclodextrin, hydroxypropyl beta-cyclodextrin, sulfated beta-cyclodextrin, 6-O-alpha-D-glucosyl-alpha-cyclodextrin, 6-O-alpha-D-glucosyl-beta-cyclodextrin, 2-hydroxy-3-trimethylammoniopropyl-beta-cyclodextrin, carboxymethyl beta-cyclodextrin, carboxyethyl beta-cyclodextrin, sulfobutyl beta-cyclodextrin, vancomycin, heparin, maltooligosaccharides, dextrin, teicoplanin, deoxy Big CHAP, and others.

One preferred embodiment uses a nonionic additive that does not form a pseudostationary phase such as micelles, microemulsion droplets, liposomes, particles, or dendrimers. An illustrative example of temperature gradient focusing with a nonionic additive system would be the use of aqueous tris-borate buffer as the fluid with gamma-cyclodextrin which is a neutral chiral selector as the additive.

Figure 7:
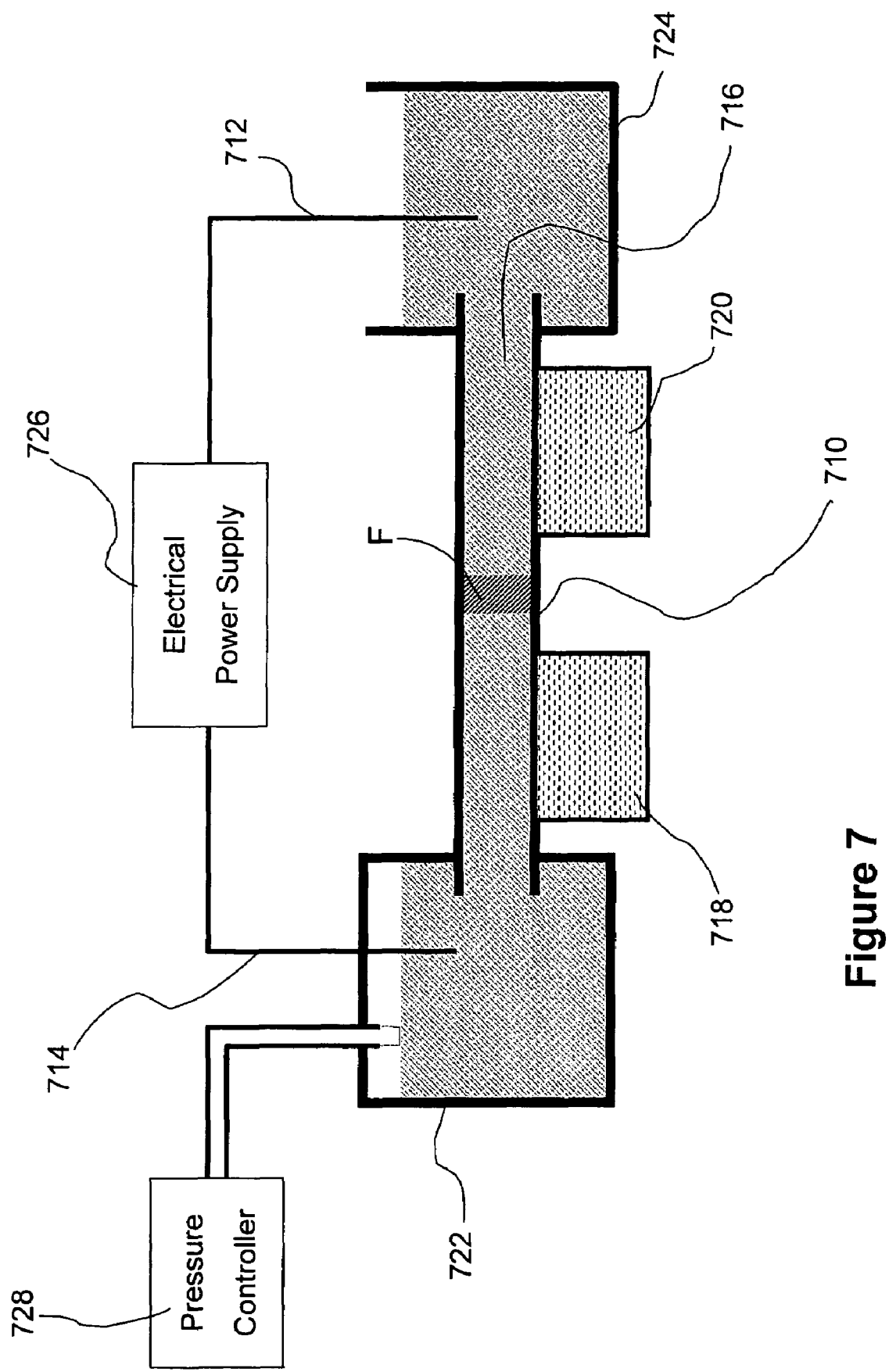
FIG. 7 is a schematic drawing of a fluidic device according to a further embodiment of the present invention.

Referring to FIG. 7, microchannel 710 is filled with a fluid 716 which contains a non-ionic chiral additive. The ends of microchannel 710 are connected to fluid reservoirs 722 and 724, which are at least partially filled with fluid. Reservoir 724 can serve as a source of materials to be focused, in which case those materials are dissolved in the fluid that is in the reservoir 724. Alternately, the materials to be focused can be dissolved in the fluid in the microchannel 710. An electrical power supply 726 is used to apply an electric field to microchannel 710 via electrodes 712 and 714. A heated block 720 and a cooling block 718 are thermally connected to microchannel 710 and provide a temperature gradient in microchannel 710 thereby generating a gradient in the electrophoretic velocity of the materials in the fluid. The counterbalancing bulk fluid flow is provided largely by the electroosmosis generated by the application of the electric field and is adjusted using a pressure controller 728 which is connected via reservoir 722 to one end of microchannel 710. The chiral additive interacts with the material or materials to be separated or focused. This interaction modifies the normal electrophoretic mobility of the material based on the interaction of the additive with the material.

As with the prior embodiments, the gradient of electrophoretic velocity of the materials can be established by the fluid having an ionic strength or pH which is temperature dependent. The velocity of the bulk fluid flow through the microchannel 710 is adjusted using the pressure controller 728 so that the bulk flow velocity has a significant component substantially aligned in the direction opposite the direction of the electrophoretic migration of one or more materials and so that the total velocity of one or more of the materials is equal to zero at region F, the focus region in the microchannel 710.

In a second chiral temperature gradient focusing embodiment, the additive used with the temperature gradient focusing forms a pseudostationary phase. The pseudostationary phase includes but is not limited to micelles, microemulsion droplets, liposomes, particles, or dendrimers, which can modify the electrophoretic mobility of the material based upon hydrophobic interactions between the material to be focused and the pseudostationary phase.

Although this method is similar to micellar affinity gradient focusing of U.S. patent application Ser. No. 10/864,485, herein incorporated by reference, this method is distinguishable in that in micellar affinity gradient focusing the electrophoretic velocity variation is due to a variation in the interaction with the additive whereas in the present method, the interaction is more typically constant and the velocity variation results primarily from a variation in the ionic strength or other property of the fluid.

It should be noted, because the fluid ionic strength is typically a critical parameter in temperature gradient focusing, preferably, the additive should not affect the ionic strength and advantageously, the additive is neutral or comprises zwitterionic molecules. If the additive is ionic, it is preferable to use a sufficiently low concentration of the additive so as to not significantly affect the conductivity of the fluid.

However, if the additive is ionic it could be used in conjunction with temperature gradient focusing to focus nonionic materials that would not be focusable without the additive. The nonionic material would effectively become ionic through its interaction with the ionic additive.

In a third chiral temperature gradient focusing form of the present invention, the materials to be focused include chiral species which are first focused without the addition of a chirally selective additive. If the materials include two or more stereoisomers of a given molecular species those stereoisomers will be focused at the same position along the fluid conduit. Once the stereoisomers are focused to a desired concentration, a chiral selector is introduced into the fluid conduit such as microchannel 710, where the additive will interact with the chiral species resulting in a shift in the focusing position of the stereoisomers and separation of the stereoisomers.

One advantage of this third chiral temperature gradient focusing embodiment is that it can provide additional information about the interaction between the additive and the materials through monitoring of the focused peaks after the introduction of the additive.

In order to provide further understanding of the present chiral temperature gradient focusing, the following example is provided which in no way limits the scope of the present invention in any way. In this example, the temperature gradient focusing was performed in a 30 μm I.D. fused silica capillary, 3 cm in length. The capillary was mechanically and thermally anchored to two copper blocks at different temperatures to create a temperature gradient along a 2 mm section approximately midway along the length of the capillary. A temperature gradient from 20° C. to 60° C. was applied.

Figure 8:
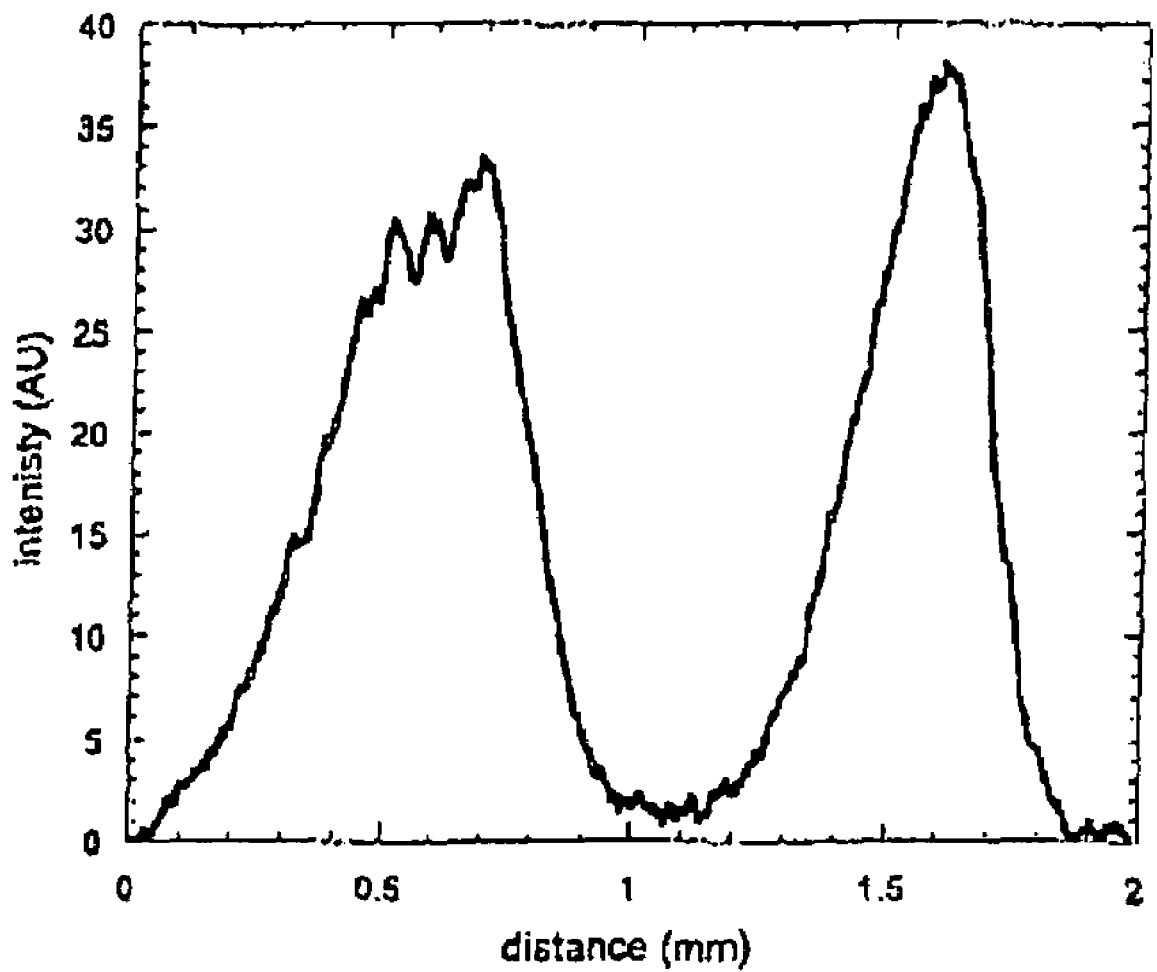
FIG. 8 is a plot depicting the concentration of two stereoisomers of a material versus distance along a microchannel in accordance with the present invention.

The fluid was 1 mol/L Tris(hydroxymethyl)aminomethane, 1 mol/L boric acid, with 20 mmol/L gamma-cyclodextrin as the chirally selective additive. A voltage of −3000 V was applied to the 20° C. end of the capillary and the 60° C. end was electrically grounded. The pressure applied to the 60° C. end of the capillary was adjusted to control the bulk flow rate so that the D and L enantiomers of glutamic acid were simultaneously focused in the 2 mm gradient section of the capillary, which was imaged using a fluorescence microscope. A plot of the measured intensity as a function of distance along the capillary is shown in FIG. 8. The two peaks are the D and L enantiomers of dansyl-glutamic acid. The fine structure near the top of the left peak is due to scratches in the plastic cladding surrounding the capillary.

An additional experiment was conducted for the enantiomeric separation of dansyl-DL-aspartic acid using 10 mm β-cyclodextrin as the chirally selective additive.

A similar procedure was also used to achieve a baseline resolved separation of two different isomers of an achiral fluorescent dye molecule, Oregon green 488 carboxylic acid (available from Molecular Probes). The separated isomers in this case are comparable to the 5- and 6-isomers of carboxyfluorescein.

A similar procedure was also used to achieve a baseline resolved separation of the fluorescently-labeled R and S enantiomers of the drug baclofen.

One of ordinary skill in the art now will readily appreciate that the present temperature gradient focusing differs from prior art methods such as sample stacking and isotachophoresis. In both cases, samples are focused or concentrated as a result of gradients in their electrophoretic velocities. In sample stacking and isotachophoresis, the velocity gradients are generated at the interfaces between solutions of different composition, and the point at which the concentration or focusing occurs is not stationary, but moves along with the bulk flow in the channel or capillary. In contrast to both sample stacking and isotachophoresis, the velocity gradients that produce material focusing in the present temperature gradient focusing result from applied temperature gradients and are stable for as long as the temperature gradient is maintained.

Further, one skilled in the art will recognized that the present temperature gradient focusing differs from isoelectric focusing techniques such as those disclosed in U.S. Pat. Nos. 3,664,939 and 5,759,370. Unlike isoelectric focusing techniques in which the pH gradient is established by using a fluid system that has a temperature dependent pH, the present temperature gradient focusing typically utilizes a fluid that has a temperature dependent ionic strength. When a temperature gradient and a voltage are applied to a microchannel, the ionic strength gradient of the fluid gives rise to a velocity gradient, which is used for focusing. As a result, a material present in the fluid is focused at a point where the material's total velocity, i.e., the sum of the electrophoretic velocity of the material and the bulk velocity of the fluid is zero. Therefore, in the present temperature gradient focusing, the pH and the isoelectric point of the material are typically not critical.

In the embodiment of the present invention that utilizes fluids with a temperature-dependent pH, and thereby uses a thermally generated pH gradient for focusing, a bulk fluid flow is applied so that rather than focusing at its isoelectric point as in isoelectric focusing, a material will focus at a position along the pH gradient where the local pH is unequal to the isoelectric point of the material.

It will now be apparent to one of ordinary skill in the art that the present microfluidic device and temperature gradient focusing method provide numerous advantages over prior devices and methods. The present device and method are simpler to implement as no imbedded electrodes or salt bridges are necessary. In addition, like isoelectric focusing, temperature gradient focusing can be used to both concentrate and separate materials, but without the disadvantages associated with isoelectric focusing.

It will now also be apparent to one of ordinary skill in the art that the present invention provides advantages over prior methods for separating enantomers which include chiral crystallization, chiral HPLC, chiral capillary electrophoresis and chiral isoelectric focusing. The advantages of the present method are especially applicable to the pharmaceutical industry where low-level enantomeric contaminants have an adverse effect.

An example of a composition containing such contaminants is thalidomide, where one enantiomer (the R) is an effective treatment for morning sickness, sleep disorders, and nausea whereas the other stereoisomer (the S) leads to phocomelia (a prenatal developmental abnormality in which the limbs of fetuses do not develop). A large number of other drugs have optical isomers, with one isomer being beneficial and the other being non-beneficial and often harmful. Thus, chiral temperature gradient focusing would be excellently suited for the detection and quantification of low-level enantiomeric impurities in pharmaceutical compounds as is critical for the prediction of the efficacy of the final preparation.

An additional advantage of the present chiral temperature gradient focusing over prior chiral capillary electrophoresis is that it is much easier to reverse the peak order. In temperature gradient focusing, the peak order can be reversed simply by changing the sign (direction) of the applied temperature gradient, the applied electric potential, and the bulk flow.

A further advantage of the present chiral temperature gradient focusing method over prior isoelectric focusing and isoelectric trapping techniques which use chirally selective additives for enantiomeric separations is provided by the use of temperature gradient focusing for focusing in that temperature gradient focusing has a number of advantages over any isoelectric focusing-based approach. For example, temperature gradient focusing can provide greater degrees of concentration enhancement than isoelectric focusing. Temperature gradient focusing is applicable to all types of ionic materials, where isoelectric focusing is applicable only to materials with a well-defined isoelectric point in the range from about 3 to about 11. In practice, this limits isoelectric focusing to use with proteins, peptides, and some chemically-modified amino acids. In addition, because the temperature gradient for temperature gradient focusing is much simpler and easier to create than the pH gradient required for isoelectric focusing, temperature gradient focusing-based chiral separations are much simpler to control and implement.

A further advantage of the present invention is provided in that only a single, continuous fluid system is required. Solid phase extraction and related preconcentration methods of the prior art require multiple fluids where one fluid is used to carry the material to the preconcentrator and a second fluid is used to release the material from the preconcentrator. Further examples of multiple fluid systems include sample stacking, field amplified injection, iosotachophoresis, and sweeping.

Further, the present temperature gradient focusing provides enhanced concentration when compared with the prior art of other single preconcentration methods.

Although the invention has been described above in relation to preferred embodiments thereof, it will be understood by those skilled in the art that variations and modifications can be effected in these preferred embodiments without departing from the scope and spirit of the invention.

What is claimed is:

1. A method for directing one or more materials in a fluid, said method comprising the steps of:
    applying an electric field to a fluid thereby causing one or more materials to move electrophoretically;
    establishing a temperature gradient in said fluid thereby generating a gradient of the electrophoretic velocity of said one or more materials;
    producing a flow of said fluid thereby changing the total velocity of said one or more materials; and
    adding an additive to said fluid thereby modifying the normal electrophoretic velocity of said one or more materials based on an interaction of said one or more materials with said additive.

2. The method of claim 1, wherein:
    said temperature gradient has a significant component substantially aligned with the electrophoretic motion of said one or more materials,
    said flow of said fluid has a significant component substantially aligned in a direction opposite a direction of said electrophoretic motion of said one or more materials, and
    adjusting magnitudes of said electric field, said temperature gradient, and said flow so that at least one of said one or more materials will accumulate or be focused at at least one position along said temperature gradient, the pH at said at least one position being unequal to the isoelectric point of said at least one of said one or more materials that are focused at said at least one position;
    whereby said step of adding an additive causes a change in the focusing position of at least one of said one or more materials.

3. The method of claim 2, wherein the pH of said fluid is temperature dependent and said temperature gradient establishes a gradient in the pH of said fluid.

4. The method of claim 2, wherein the ionic strength of said fluid is temperature dependent and said temperature gradient establishes a gradient in the ionic strength of said fluid.

5. The method of claim 4, wherein at least two of said one or more materials being initially spatially mixed within said fluid are separated.

6. The method of claim 4, wherein said one or more materials are selected from the group consisting of fluorescent dyes, ions, amino acids, peptides, proteins, nucleic acids, cells, and colloidal particles.

7. The method of claim 4, wherein said fluid is selected from the group consisting of ionic aqueous solutions, ionic non-aqueous solutions, aqueous buffer solutions, and mixtures of aqueous and non-aqueous solutions.

8. The method of claim 4, wherein said electric field is applied using a set of components comprising an electrical power supply and two or more electrodes contacting said fluid.

9. The method of claim 4, wherein the temperature gradient is one of linear and non-linear.

10. The method of claim 4, wherein the temperature gradient is one of monotonic and non-monotonic.

11. The method of claim 4, wherein said step of establishing a temperature gradient comprises applying an electric current to the fluid to produce the temperature gradient by Joule heating.

12. The method of claim 4, wherein said step of establishing a temperature gradient comprises supplying thermal energy to said fluid via a heated block.

13. The method of claim 4, wherein said step of establishing a temperature gradient comprises removing thermal energy from said fluid via a cooled block.

14. The method of claim 4, wherein said flow is generated by electroosmosis.

15. The method of claim 4, wherein said flow is generated by pressure gradients.

16. The method of claim 4, wherein said flow is generated by a combination of electroosmosis and pressure gradients.

17. The method of claim 4, wherein said additive comprises a chiral selector.

18. The method of claim 17, wherein said chiral selector is selected from the group consisting of alpha-cyclodextrin, beta-cyclodextrin, gamma-cyclodextrin, heptakis-O-methyl beta-cyclodextrin, heptakis(2,6-di-O-methyl) beta-cyclodextrin, heptakis(2,3,6-tri-O-methyl) beta-cyclodextrin, hydroxyethyl beta-cyclodextrin, hydroxypropyl beta-cyclodextrin, sulfated beta-cyclodextrin, 6-O-alpha-D-glucosyl-alpha-cyclodextrin, 6-O-alpha-D-glucosyl-beta-cyclodextrin, 2-hydroxy-3-trimethylammoniopropyl-beta-cyclodextrin, carboxymethyl beta-cyclodextrin, carboxyethyl beta-cyclodextrin, sulfobutyl beta-cyclodextrin, vancomycin, heparin, maltooligosaccharides, dextrin, teicoplanin, and deoxy Big CHAP.

19. The method of claim 4, wherein said additive comprises a nonionic additive.

20. The method of claim 4, wherein said additive does not form a pseudostationary phase.

21. The method of claim 4, wherein said additive forms a pseudostationary phase.

22. The method of claim 21, wherein said pseudostationary phase is selected from the group consisting of micelles, microemulsion droplets, liposomes, particles and dendrimers.

23. The method of claim 21, wherein said additive is selected from the group consisting of anionic surfactants, cationic surfactants, and nonionic surfactants.

24. The method of claim 4, wherein the interaction of a first stereoisomer of one of said one or more materials with said additive is stronger than the interaction of a second stereoisomer of said one of said one or more materials with said additive, thereby allowing the separation of said first stereoisomer from said second stereoisomer.

25. The method of claim 4, wherein said step of applying an electric field, said step of establishing a temperature gradient, and said step of producing a bulk flow comprise using an electrical power supply to apply a voltage to said fluid, and wherein the electric field provided by said electrical power supply causes the electrophoretic motion of said one or more materials, a flow of electric current in said fluid thereby generating said temperature gradient by Joule heating, and electroosmosis of said fluid thereby producing said flow of said fluid.

26. The method of claim 4, wherein said step of applying an electric field and said step of producing a bulk flow comprise using an electrical power supply to apply a voltage to said fluid, and wherein the electric field provided by said electrical power supply causes the electrophoretic motion of said one or more materials, and electroosmosis of said fluid thereby producing said flow of said fluid.

27. The method of claim 4, wherein said steps of applying an electric field, establishing a temperature gradient, and producing a flow are implemented first, thereby focusing said one or more materials into at least one group, said at least one group each containing all of the extant stereoisomers of each of said one or more materials, respectively;

after which, said step of adding an additive is implemented, whereby said stereoisomers of one or more of said at least one group are refocused at different positions along said temperature gradient and are thereby separated.

28. The method of claim 4, wherein said fluid is supplied as a continuous single fluid flow.

29. The method of claim 4, further comprising the step of collecting said at least one of said one or more materials after it has been focused.

\* \* \* \* \*

UNITED STATES PATENT AND TRADEMARK OFFICE
CERTIFICATE OF CORRECTION

PATENT NO. : 7,572,357 B2  Page 1 of 1
APPLICATION NO. : 11/039955
DATED : August 11, 2009
INVENTOR(S) : Ross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1236 days.

Signed and Sealed this

Seventh Day of September, 2010

David J. Kappos
*Director of the United States Patent and Trademark Office*